United States Patent [19]
Reintgen

[11] Patent Number: 6,153,388
[45] Date of Patent: Nov. 28, 2000

[54] METHOD OF DETERMINING MELANOMA MICROMETASTASIS USING TYROSINASE

[75] Inventor: Douglas S. Reintgen, Tampa, Fla.

[73] Assignee: University of South Florida, Tampa, Fla.

[21] Appl. No.: 09/245,822

[22] Filed: Feb. 5, 1999

Related U.S. Application Data

[63] Continuation of application No. 08/878,153, Jun. 18, 1997, abandoned, which is a continuation of application No. 08/330,359, Oct. 27, 1994, abandoned.

[51] Int. Cl.[7] .................................................. C12Q 1/68
[52] U.S. Cl. .......................... 435/6; 435/912; 435/91.51; 536/24.31; 536/24.33
[58] Field of Search .......................... 435/6, 91.2, 91.51; 536/24.31, 24, 33

[56] References Cited

FOREIGN PATENT DOCUMENTS 2260811  4/1993  United Kingdom .

OTHER PUBLICATIONS

Heller et al. Annals of Plastic Surgery 28:74–77, 1992.

Morton et al. Arch Surgery. 127:392–399, Apr. 1992.

Van der Velde–Zimmermann et al. American Journal of Pathology. 149: 759–764, Sep. 1996.

*Primary Examiner*—Carla J. Myers
*Attorney, Agent, or Firm*—Kohn & Associates

[57] ABSTRACT

A highly sensitive method to detect melanoma micrometastasis by examining lymph nodes for the presence of tyrosinase messenger RNA. In a preferred mode, this is accomplished using the combination of reverse transcription and double round polymerase chain reaction (RT-PCR). The amplified samples are examined on a 2% agarose gel and tyrosinase is seen as a 207 base pair fragment. The lymph nodes examined are determined using pre- and intra- operative node mapping.

9 Claims, 3 Drawing Sheets

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "Primer HTYR1"

(xi) SEQUENCE DESCRIPTION: SEQ ID NO:1:

TTGGCAGATT GTCTGTAGCC                            20

(2) INFORMATION FOR SEQ ID NO:2:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "Primer HTYR2"

(iv) ANTI-SENSE: YES (xi) SEQUENCE DESCRIPTION: SEQ ID NO:2:

AGGCATTGTG CATGCTGCTT                            20

(2) INFORMATION FOR SEQ ID NO:3:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "Primer MEL1"

(xi) SEQUENCE DESCRIPTION: SEQ ID NO:3:

GTCTTTATGC AATCGAAC                              18

(2) INFORMATION FOR SEQ ID NO:4:

(i) SEQUENCE CHARACTERISTICS:
      (A) LENGTH: 18 base pairs
      (B) TYPE: nucleic acid

```
            (C) STRANDEDNESS: single
            (D) TOPOLOGY: linear (ii) MOLECULE TYPE: other nucleic acid
            (A) DESCRIPTION: /desc = "Primer MEL2"

(iv) ANTI-SENSE: YES (xi) SEQUENCE DESCRIPTION: SEQ ID NO:4:

GCTATCCCAG TAAGTGGA                                                      18
```

METHOD OF DETERMINING MELANOMA MICROMETASTASIS USING TYROSINASE

CROSSREFERENCE TO RELATED APPLICATIONS

This Application is a continuation of U.S. Ser. No. 08/878,153, filed on Jun. 18, 1997 now abandoned, which was a continuation of U.S. Ser. No. 08/330,359, filed on Oct. 27, 1994, now abandoned, which are herein incorporated by reference.

BACKGROUND

Malignant melanoma is a form of skin cancer that can develop from melanocytes, cells that are capable of forming melanin, a dark-brown to black pigment. Most melanomas develop from a previous mole over a period of several months or years and occur most commonly in fair-skinned people that are intolerant to sunlight. There are several distinct types of melanomas. Prognosis depends on the kind of melanoma, its depth of invasion, its location, and the age and health of the patient.

According to new statistics, malignant melanoma could become a lethal epidemic in the next decade. In 1993, 32,000 people in the United States developed melanoma, and 6,420 died from it. Exactly why the rate of skin cancer is growing so rapidly is not known although accumulating evidence suggests that sun exposure and the thinning ozone layer play a major role.

Patients who receive early diagnosis and treatment have a high chance of survival. Most patients in the early stages of melanoma undergo surgery to remove the primary tumor. Patients with locally advanced or metastatic disease usually also undergo some type of chemotherapy and may also receive radiation therapy although radiation is not usually very effective against melanoma. Other treatments include cytotoxic drugs, treatment with immunological substances and autologous (self) bone marrow transplant to enhance the patient's immune system.

Melanoma surgical care is undergoing change with the advent of pre-operative and intra-operative mapping techniques that identify the sentinel node of the lymphatic basin. Lymphoscintigraphy performed on a group of patients in a recent study [Redefinition of Cutaneous Lymphatic Drainage with the Use of Lymphoscintigraphy for Malignant Melanoma; Norman, J, Reintgen, D S, et al.; Amer. J. Surg.; 162; November 1991; 432 (6)] has demonstrated that the lymphatic drainage pathways identified in classical anatomical studies differ significantly from the results obtained from in vivo models. The new study demonstrates that there are much larger areas of ambiguous drainage than previously reported. Further, the study demonstrates a high level of individuality of cutaneous lymphatic flow. It is estimated that over 50% of all lymph node dissections for intermediate thickness melanomas may be misdirected if pre-operative mapping is not performed.

Histopathologists usually examine and determine the extent of melanomas of the skin by measuring the thickness of the tumor and the level of penetration into the skin measured in millimeters from the top of the granular cell layer to the deepest point of tumor extension. Breslow [Breslow, A., Tumour Thickness, Level of Invasion and Node Dissection in Stage 1 Cutaneous Melanoma, Ann. Surg 1975; 182: 572–75] has developed a commonly used grading system for melanoma thickness. This is regarded as the most important morphological variable for determining prognosis in patients with localized disease. Breslow grouped tumor thickness into three categories; thin [<0.76 mm], intermediate [0.76 mm–4.00 mm] and thick [>4.00 mm]. Recent reports however, indicate certain problems associated with assessing Breslow thickness [Measuring melanomas (editorial) The Lancet; 338; Aug. 10, 1991; 351(2)]. Level of invasion, classified by Clark [Clark, W. H. Jr., From, L.; Bernardino, A.; Mihm, M. C.; The Histogenesis and Biological Behaviour of Primary Human Malignant Melanomas of the skin; Cancer Res. 1969; 29; 705–26] into five categories on the basis of the normal anatomy of the dermis carries less prognostic weight but is usually also included in histopathological reports.

Melanoma may be localized (Stage 1 and 2 disease) or the cancer may have spread (metastasized) to other parts of the body (Stage—3 or 4 disease). Researchers have long sought a quick, simple to use, inexpensive test to determine the presence of metastatic melanoma.

There are a number of methods that are used in the clinical laboratories to determine whether the melanoma is metastatic. Currently available tests are based on the light microscopic examination of samples of bone marrow, lymph tissues or other tissue samples.

Morphological distinctions exist between tumor cells and lymphocytes (white blood cells found in large numbers in the blood and the lymph). However, it can be difficult to distinguish melanoma cells from normal lymphocytes or other normal cells, especially when only a small proportion of the cells are abnormal or the aberrant cell is not apparent. The problem becomes even more severe when the melanoma is in the early stages of metastasis and only a very small number of tumor cells are present in the blood, lymph node or bone marrow.

Another problem with the standard procedure for examining lymph nodes for tumor involvement is the quantity of tissue removed for sampling. The examination of 1 or 2 sections from the center of the lymph node samples only about $\frac{1}{1000}$ of the tissue submitted for pathological examination.

Routine histological examination and histologic staining for the evaluation of metastatic melanoma are currently available in many hospitals. However, histopathological examination is not sufficiently sensitive to adequately diagnose early metastasis of melanoma. False negative results may be obtained because of very few tumor cells in the pathologic samples. This is borne out by the fact that approximately 25 to 33 percent of the patients who are histologically node negative will have recurrent tumors and die of their disease. Despite good prognostic factors, metastases are missed and patients die of their disease.

The histopathological approach routinely underestimates the number of patients with metastases. The standard histopathology interpretation with hematoxylin-eosin staining (H&E staining and light microscopy evaluation) routinely used for the detection of metastatic tumor cells in tissue has a sensitivity of 1 in $10^4$ normal cells. The rate limiting factor of routine histopathology examination is the number of sections of the lymph node made, stained and examined; the examination becomes limited when only $\frac{1}{1000}$ of the tissue submitted for processing is ordinarily examined.

Methods such as serial sectioning and immunohistochemistry are used to increase the sensitivity of the tests. Recently, marker tests relying on antibodies specific to components on the cell surface of tumor cells have been developed. In general, these antibodies react with glycoproteins or gangliosides on the surface of the target cell. When such glycoproteins or gangliosides are present in abnormally large amounts or are present in conditions where they are not usually found, they are a signal that abnormal cells are present or are circulating.

If the tissue being evaluated for the presence of metastatic melanoma appears to be pathologically suspicious upon inspection, immunohistochemical staining with antibodies against S-100 protein or HMB-45 melanoma antigen can help to confirm the diagnosis. Unfortunately, these markers are not unique to cancer cells and their usefulness depends upon what is tested and the number of sections examined.

Even though the techniques have been available for a number of years and have been reported to increase the yield of occult metastases by a factor of 2 these assays have not been incorporated into the routine screening of lymph node sections in the community. The time and expense involved prevents them from being used routinely and they will never be widely adopted.

An additional problem with these methods is that they are based on finding changes in morphologic features and/or expression of specific proteins, methods that are not always accurate and can lead to ambiguous results. Furthermore, even such immunohistological methods are not sufficiently sensitive to properly diagnose early metastasis of melanoma.

As stated above, most tests are based on the examination of samples of blood, lymph tissues or other tissues of the body to determine the presence of melanoma cells. The presence or absence of lymph node metastases in patients with malignant melanoma is the single most powerful prognostic factor for predicting survival.

Clinically, the management and the five year survival rate for Stage III melanoma patients with regional lymph node involvement are different from that of Stage I or II patients. Either immunotherapy or chemotherapy is needed besides surgical dissection. So the early detection of metastasis in lymph nodes is very important for the patient classification, treatment and prognosis.

As an example of the importance of proper staging, the 5 year survival for Stage 3 melanoma patients with regional nodal involvement is 50% decreased compared to the survival of node negative patients. Adjuvant therapies have been attempted in order to increase the survival of the Stage 3 melanoma patient who has no evidence of disease but where the disease is likely to recur. Theoretically, the accurate and early detection of metastatic disease would allow those Stage 3 patients to be enrolled in the adjuvant trials earlier when systemic tumor burden is small and the likelihood of success is better.

The minute quantities of target cells present in lymph tissue makes it imperative that more sensitive techniques of selectively increasing the population of target cells be used. One technique uses cell culture methods to increase the population of target cells. [Heller, Reintgen, et al., Arch. Surg. 1991:126:1455–1460]

In one novel cell culture method for detecting micrometastases, the entire node is sampled by placement in tissue culture, much different than routine histologic examination that samples at most 0.1% of the submitted tissue. With this sensitive cell culture technique, over twenty percent of Stage 1 and 2 melanoma patients can be upstaged to Stage 3 disease (nodal metastases) when compared to routine histologic examination. Patients who were histologically node negative but culture node positive had a poorer disease free survival when compared to those patients who were node negative by both methods. Although this test offers a more sensitive method than histologic examination, on average it takes 4–6 weeks to obtain definitive results and has limited applicability to the community hospital setting. Furthermore, the tissue culture technique is fairly laborious.

Since melanocytes are not normally present in peripheral blood, bone marrow or lymph nodes, the presence of such cells in these immune system components is an indication that there are metastatic melanoma cells present. In addition to the presence of the malignant cells themselves, parts or artifacts of the cells presence may also be utilized to determine the presence of the target cells. Thus the presence of mRNA demonstrating the active expression of genes not expressed by cells normally occurring in peripheral blood, bone marrow or lymph tissue or the presence of the protein itself could be utilized as the indicator of the presence of the disease.

These diagnostic techniques are dependent upon 1) the presence of markers such as cells, cell parts or cell proteins that are not present in the sample in the absence of disease and 2) a method, sufficiently sensitive and specific, of indicating the presence of the chosen marker.

Through the work of a series of experimenters it has now been determined that the presence of mRNA transcribed from the tyrosinase gene is a useful indicator that there are metastatic melanoma cells present.

Tyrosinase is a copper-based oxidoreductase that catalyzes the oxidation of tyrosinase to dopa and the oxidation of dopa to dopaquinone. These are the first two steps in the biosynthesis of melanin, the pigment in normal skin. Tyrosinase is a key and rate limiting enzyme during melanin synthesis in melanocytes and melanoma cells. Since tyrosinase is not normally found in lymph nodes, the presence of tyrosinase and, by extension, melanin containing cells in lymph node sections is good evidence that metastatic melanoma cells are present.

Another diagnostic technique would utilize the occurrence of active transcription of the tyrosinase gene as an indicator of the presence of metastatic melanoma cells. If messenger RNA for tyrosinase is found in the lymph node sample, then that finding would indicate the active transcription of the tyrosinase gene and the presence of tyrosinase which in turn would indicate the presence of a melanocyte.

The most significant problem associated with these techniques is that in each case the target is present in such minute quantities that it is difficult if not impossible to separate any signal resulting from the presence of the target from the background present in the test system.

The invention of the polymerase chain reaction has provided a technique for rapidly and easily increasing the quantity of a specific DNA segment from a mixture containing a multitude of different DNA segments. Since PCR works to multiply only DNA segments, the target to be amplified must be in the form of DNA.

In actively reproducing cells multiple copies of messenger RNA (mRNA) for proteins expressed by that cell are likely to be present. Thus, the tyrosinase mRNA is a candidate for a diagnostic test for the presence of melanocytes.

In order to utilize the mRNA of tyrosinase in a PCR reaction, the mRNA must be converted to DNA. This can be accomplished by using reverse transcriptase. Reverse transcriptase is an enzyme that is capable of reading a strand of RNA and producing a strand of complementary DNA (cDNA).

In 1991, Smith and colleagues reported a procedure using reverse transcriptase and polymerase chain reaction for determining the presence of melanoma cells in peripheral blood. [Smith, B. et al., Detection of melanoma cells in peripheral blood by means of reverse transcriptase and polymerase chain reaction; Lancet 1991; 338; 1227–29]. The procedure is based on the principle that the haematogenous spread of cancer influences the outcome of the disease for most patients. Since the number of circulating tumor cells in the blood is very small techniques for their detection are required to be both highly sensitive and highly specific.

Smith et al.'s procedure targets a gene-specific product of genes which are active in melanocytes but not in the cells normally found in peripheral blood. The procedure uses reverse transcriptase to prepare complementary DNA from messenger RNA contained in peripheral blood samples and polymerase chain reaction to amplify the target, in this case the cDNA made from the mRNA for tyrosinase.

This procedure is a significant advance over prior methods but it has several problems associated with it. The procedure does not allow the clinician to localize the site of the metastases; the volume of circulating blood is so large that the concentration of tumor cells in peripheral blood is inherently minimized; and the test is not useful in patients with apparently localized disease in whom peripheral blood cells may be few or absent. In addition, the most common site of melanoma metastases is regional nodes and the clinical relevance of finding circulating tumor cells is blood has not been proven. For instance, studies have shown that tumor cells can be routinely found in the peripheral circulation during operative procedures, but since these patients have a similiar disease progression to those in which no tumor cells can be demonstrated, it is more an academic rather than a clinically relevant finding.

Most importantly, the Smith technique does not work on lymph tissue. When attempts were made to utilize the Smith process on lymph tissue the result was always positive even in the absence of melanoma (false positives).

Thus there continues to exist the need for a fast, effective test for determining the presence of metastasized melanoma. In addition there exists a need for determining the localization of the metastatic tumor, the involvement of the patients lymph system since the lymph system is the first site of metastatistic disease and the determination of the involvement of other regions of the body. There is also the need for a test to determine whether apparently localized disease has metastasized to the lymph system, to develop a highly sensitive method to detect micrometastases by examining lymph nodes for the presence of tyrosinase messenger RNA and to determine whether a metastatic tumor is present even though it has not yet lodged in other locations in the patients body. Yet another problem relates to determining the quantity of metastasized cells present in a sample as an indicator of the advancement of the disease.

SUMMARY

We have discovered a assay which is able to detect 1 malignant melanoma cell in a background of 1 million normal lymphocytes in lymph node tissue. This new diagnostic test will enable clinicians to accomplish multiple functions with a single test procedure.

Most importantly, it will enable the diagnostician to determine the presence of micrometastases in the lymph tissue of patients. It will allow the proper and accurate staging of the patient. It will permit the physician to determine the effect of different primary and adjuvant therapies. It will permit the determination of prognosis for the patient's survival.

The procedure will permit the determination of lymph node involvement and spread of the disease. Coupled with the new lymphatic mapping techniques and sentinel node harvesting, the assay will permit the selective dissection of peripheral nodes to determine the relative penetration of the melanoma into the lymph system. It will help in determining whether patients harboring metastatic tumors in regional nodes also have tumors disseminated beyond the nodes. It will allow determination of the quantity of metastasized cells present in a sample as an indicator of the advancement of the disease.

The assay is accomplished using the combination of reverse transcriptase and double round polymerase chain reaction. (RT-PCR). The amplified samples are examined on a 2% agarose gel. Tyrosinase cDNA, if present, is seen as a 207 base pair fragment.

RT-PCR is a highly sensitive and specific method. It is economical and relatively simple. Many samples can be tested at the same time and the entire procedure can be completed in a couple of days. Since the complementary DNA (cDNA) prepared by the reverse transcriptase represents only the actively expressed genes and this cDNA sequence is exponentially amplified by the polymerase, this method is not only highly sensitive but also very specific.

This more sensitive method for the identification of occult metastases does more than just stage shift; it identifies a subgroup of the melanoma population who have the most to benefit from the effective adjuvant therapies. This procedure is able to detect tyrosinase mRNA in all pathology positive specimens. (Samples 30–37, Table 1) In spiking experiments, the technology is able to identify one abnormal melanoma cell in a background of one million normal lymphocytes, a sensitivity of 2 log greater than routine histology with immunohistochemical staining, thus demonstrating that the RT-PCR assay is more sensitive than routine methods.

Coupled with new techniques for determining sentinel node involvement and in more accurate methods for determining lymphatic drainage basins, this multi-step assay permits a surprisingly high degree of accuracy in localizing and staging metastatic disease.

DETAILED DESCRIPTION

Figure 1:
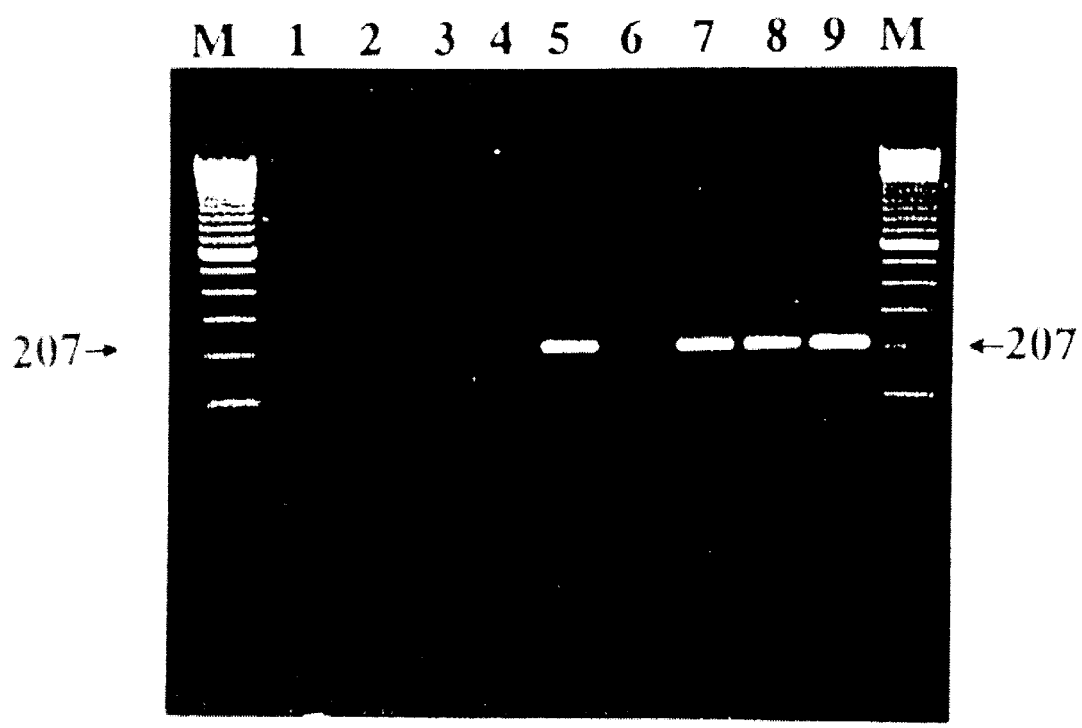
FIG. 1 shows the tyrosinase RT-PCR2 results from patient samples and cell lines. Lane 1, blank. Lane 2, negative control from breast cancer cell line T47D (Sample #47). Lane 3 and 4, samples from node negative melanoma patients (Sample #'s 12–13). Lane 5, sample from primary colon cancer (Sample #41). Lane 6, sample from primary breast cancer (Sample #38). Lane 7 to 8, samples from node negative melanoma patients (Sample #'s 14–15). Lane 9, positive control from melanoma cell line SK-Mel-28 (Sample #48).

The diagnostic procedure begins when the patient is examined by the attending physician. When the physician determines the presence of questionable tissue, a biopsy sample is taken and sent to the laboratory for determination. When the patient has been determined to have melanoma, additional testing is conducted to determine whether the melanoma has metastasized. The present invention pertains to the methods used to determine the presence of metastatic melanoma and the extent of the metastasis.

Samples of lymph tissue are taken from the lymph basin of the patient using pre-operative and intra-operative mapping techniques. Unlike other procedures only small quantities of tissue are needed. The lymph tissue is taken from those lymph nodes that have been determined by the diagnostician to be most likely to be involved in the metastasis (in particular, the sentinel node which is defined as the first node in the basin into which the primary site drains). Various mapping procedures may be utilized to determine the correct nodes to sample.

In our procedure the patient is subjected to lymphoscintigraphy to determine all drainage basins at risk for metastatic disease and sentinel flow study is performed to mark the location of the sentinel node in relation to the rest of the basin. The procedure uses 1% lymphozurin injected intradermally around the site of the primary lesion to perform intra-operative mapping. After allowing time for the dye to travel to the nodal basin, an incision is made and the afferent blue staining lymphatic identified and followed to a blue staining sentinel node.

Other techniques set forth in the literature may also be utilized. One method utilizes technetium sulfur colloid to determine the direction of the lymphatic flow and the location of the sentinel node. The area surrounding the primary lesion is injected with this radioactive substance and its drainage pattern is established. Samples are then removed from the nodes in the drainage basin and subjected to the assay described in this specification.

Once the drainage basin has been determined and mapped, tissue is removed from the sentinel node, the node most likely to be the site of metastasis. Depending on the circumstances the physician may remove tissue from one or more additional nodes. The presence of tissue from several nodes will allow the physician to map the progress of the disease both by the presence or absence of metastasized cells or by the quantity of cells present.

For the first time the physician can determine not only the presence of the disease but a clear indication as to its localization and quantification. Once the presence, location and quantification of the tumor cells have been determined the physician may intervene as may be appropriate. For instance, if the sentinel node is found to harbor melanoma metastases, the patient is a candidate for complete node dissection. For the first time, melanoma patients can obtain highly sensitive and accurate staging with minimal morbidity by combining lymphatic mapping techniques with the PCR assay for occult metastases. The novel combination of these two procedures has never been utilized for clinical purposes.

Our procedure requires specimens of the lymph node tissue of a patient suspected of having metastatic melanoma. Although our technique could in theory be applied to other tissues, other tissues would not provide the quantity of information available from lymph tissue, as to the location of the disease or to the presence of metastasized cells that may not yet have lodged in ancillary tissue.

The cellular lymph material is treated in conventional ways to disrupt the cells. Once the cells are disrupted, the RNA present is separated from cellular material and DNA. We prefer to use a commercial kit to accomplish this step; the RNA STAT-60 kit is useful and convenient. The lymph cells+phenol+guanidium thiocyanate are homogenized in a needle; chloroform is added; when phase separation occurs, the aqueous phase containing the RNA is removed. The RNA is precipitated, washed and resolubilized.

The total RNA is combined with deoxynucleotide triphosphate in a buffer with reverse transcriptase and an antisense outer primer, HTYR2, (SEQ ID No:2) a primer devised from the sequence for tyrosinase cDNA (Smith et al., infra). The mixture is incubated for a period of thirty minutes or longer, denatured, and placed in ice.

The following polymerase chain reaction mixture for the extension of outer primer to obtain 284 bp cDNA fragment may be prepared immediately before use and directly added into each reverse transcription reaction tube: PCR buffer (10 mM Tris-HCl, 50 mM KCl, pH 8.3), $MgCl_2$, distilled water, AmpliTaq DNA polymerase (Perkin-Elmer-Cetus Corp. or Promega (Fisher Scientific)), and sense outer primer (HTYRI) (SEQ ID No:1). Heating at was followed by a two-step PCR for 30 cycles.

The first round of PCR yields a 284 bp DNA fragment. In some samples the 284 bp fragment was visible on 2% agarose gel after the first round PCR but the density of the band was very low.

Our preferred detection procedure utilizes two rounds of PCR amplification. The product of the first polymerase chain reaction is reamplified with nested primers (anti-sense MEL1 (SEQ ID No:3) and sense MEL2 (SEQ ID No:4) to obtain 207 bp cDNA fragment. Since the sensitivity of the assay is greatly increased by using nested primers and a double amplification, we prefer to use a double round PCR amplification.

The sequence of the primers is:
HTYRI (SEQ ID No:1): TTGGCAGATTGTCTGTAGCC
HTYR2 (SEQ ID No:2): AGGCATTGTGCATGCTGCTT
MEL1 (SEQ ID No:3): GTCTTTATGCAATGGAAC
MEL2 (SEQ ID No:4): GCTATCCCAGTAAGTGGA β-actin cDNA fragment was amplified using the identical method. However, the primers for tyrosinase gene were replaced by β-actin gene primers. β-actin mRNA was successfully reverse transcribed and amplified from all the tyrosinase gene negative samples. This indicates that the RNA in all the samples was undegraded.

Double PCR without RT (NO-RT-PCR) was carried out to ensure that the amplified sequence was from cDNA but not from genomic DNA. Specimens with detectable tyrosinase gene were examined by NO-RT-PCR. None of these was positive, indicating that the samples did not contain genomic DNA.

Mapping with restriction enzymes was used to determine if the PCR product was obtained from tyrosinase mRNA.

The sequence of tyrosinase mRNA is known and the size of fragments obtained with these enzymes can be predicted. The results of our treatment are the same as the base pair length anticipated for the tyrosinase gene. Thus, restriction enzyme mapping confirms that the RT-PCR2 products are from tyrosinase gene.

Our invention is further demonstrated by the following non-limiting examples.

EXAMPLE 1

Node Specimens

Tissue was obtained from the regional lymph nodes of 29 clinically negative (no metastases) melanoma patients (intermediate thickness melanoma, Stages 1 and 2), (Samples #'s 1–29), 3 patients with primary melanoma in which the primary tumor was available for sampling (Sample #'s 30–32), 5 patients with grossly positive nodal disease for metastatic melanoma (Samples #'s 33–37), 6 patients with other types of cancer (Sample #'s 41–46) and 3 patients who were cancer free (Sample #'s 38–40). One-half of the lymph node or tissue was sent for standard pathological evaluation, the other half retained for examination by the new procedure. An average of 5 nodes per patient were examined.

EXAMPLE 2

Control Pathological Evaluation

As a control one-half of each lymph node or tissue from Example 1 was subjected to standard pathological evaluation. The procedure involved making one or two sections of the central cross-section of the node and staining with H&E.

Routine histopathology detected melanoma cells in lymph nodes from 11 of the 29 clinically assessed melanoma patients and found no melanoma cells in the lymph nodes of eighteen patients. Eight lymph nodes were histopathologically negative, but PCR positive.

In the eight lymph nodes which were histopathologically negative, but PCR positive, the original blocs were obtained from the lymph node examination, serial sectioned and stained with immunoperioxidase staining. Standard immunoperoxidase staining techniques with antibodies for S-100 protein and HMB-45 antibody (Biogene, CA) were performed using aminoethylcarbazole (AEC) chromagen as a developer in an attempt to find the melanoma cells.

In the eight patients who were histopathologically negative, but PCR positive, no melanoma cells in the nodal tissue could be identified by immunoperoxidase techniques that were not identified by routine histopathology. Numerous nodal dendritic cells were labeled by S-100 protein antibody in each case, but the cells did not have the cytologic features of malignant cells and the sections were negative with the HMB-45 antibody.

TABLE 1

| Patient # | Sample Type | Cancer Type | Histo-pathology Results (Control) | Histo-pathology Results with S-100 Staining | PCR Results | β-actin Results |
|---|---|---|---|---|---|---|
| 1 | lymph node | melanoma | + | + | + | + |
| 2 | lymph node | melanoma | + | + | + | + |
| 3 | lymph node | melanoma | + | + | + | + |
| 4 | lymph node | melanoma | + | + | + | + |
| 5 | lymph node | melanoma | + | + | + | + |
| 6 | lymph node | melanoma | + | + | + | + |
| 7 | lymph node | melanoma | + | + | + | + |
| 8 | lymph node | melanoma | + | + | + | + |
| 9 | lymph node | melanoma | + | + | + | + |
| 10 | lymph node | melanoma | + | + | + | + |
| 11 | lymph node | melanoma | + | + | + | + |
| 12 | lymph node | melanoma | − | − | + | + |
| 13 | lymph node | melanoma | − | − | + | + |
| 14 | lymph node | melanoma | − | − | + | + |
| 15 | lymph node | melanoma | − | − | + | + |
| 16 | lymph node | melanoma | − | − | + | + |
| 17 | lymph node | melanoma | − | − | + | + |
| 18 | lymph node | melanoma | − | − | + | + |
| 19 | lymph node | melanoma | − | − | + | + |
| 20 | lymph node | melanoma | − | − | − | + |
| 21 | lymph node | melanoma | − | − | − | + |
| 22 | lymph node | melanoma | − | − | − | + |
| 23 | lymph node | melanoma | − | − | − | + |
| 24 | lymph node | melanoma | − | − | − | + |
| 25 | lymph node | melanoma | − | − | − | + |
| 26 | lymph node | melanoma | − | − | − | + |
| 27 | lymph node | melanoma | − | − | − | + |
| 28 | lymph node | melanoma | − | − | − | + |
| 29 | lymph node | melanoma | − | − | − | + |
| 30 | 1° melanoma | melanoma | + | + | + | + |
| 31 | 1° melanoma | melanoma | + | + | + | + |
| 32 | 1° melanoma | melanoma | + | + | + | + |
| 33 | lymph node | melanoma* | + | + | + | + |
| 34 | lymph node | melanoma* | + | + | + | + |
| 35 | lymph node | melanoma* | + | + | + | + |
| 36 | lymph node | melanoma* | + | + | + | + |
| 37 | lymph node | melanoma* | + | + | + | + |

TABLE 1-continued

| Patient # | Sample Type | Cancer Type | Histo-pathology Results (Control) | Histo-pathology Results with S-100 Staining | PCR Results | β-actin Results |
|---|---|---|---|---|---|---|
| 38 | breast tissue | none | – | N.A. | – | + |
| 39 | lymph node | none | – | N.A. | – | + |
| 40 | breast tissue | none | – | N.A. | – | + |
| 41 | 1°colon cancer | colon | –** | N.A. | – | + |
| 42 | lymph node | colon | –** | N.A. | – | + |
| 43 | 1° colon cancer | colon | –** | N.A. | – | + |
| 44 | lymph node | colon | –** | N.A. | – | + |
| 45 | breast tissue | breast | –** | N.A. | – | + |
| 46 | lymph node | breast | –** | N.A. | – | + |
| 47 | T47D*** | breast cancer cell line | –** | N.A. | – | + |
| 48 | MEL-28*** | melanoma cell line | + | + | + | + |
| 49 | K562*** | lymphoid cell line | – | N.A. | – | + |

In Table 1:

+ indicates the presence of melanoma cells.

– indicates the absence of melanoma cells.

\* refers to metastatic melanoma in a lymph node that was grossly appparent and histologically confirmed.

\*\* refers to negative finding of melanoma cells in the specimens by routine histology. All specimens examined were positive for their respective tumor (i.e. breast or colon or lymphoid).

\*\*\* refers to commercially available cell lines.

The first 29 samples were from clinically negative nodes of melanoma patients; samples 33–37 were from clinically positive (indicated presence of metastasized cells) nodes of melanoma patients; samples 38–40 were cancer free patients; samples 41, 43 were from colon primary tumors and sample 42–44 were from lymph nodes of colon cancer patients. Sample 45 was from a primary breast tumor and sample 46 was from a lymph node that contained metastatic breast cancer.

Summarizing the results recorded in Table 1:

1. All specimens tested were positive with the β-actin control suggesting that in all specimens mRNA was present for amplification.

2. The positive control cell line MEL-28 (Sample #48) was always positive with the PCR assay. Likewise, all clinically node negative, but histologically node positive melanoma patients were also PCR positive. (Sample #'s 1–11) In addition, the 3 primary melanoma patients tested (Sample #30–32) and the 5 patients with grossly positive nodal disease (Sample #'s 33–37) were positive histologically and with the PCR assay.

3. Tissue from patients without melanoma or other types of cancer (either primary or metastatic) (Sample #'s 38–46) were always histologically negative and PCR negative.

4. 10 patients (Sample #'s 20–29) were clinically node negative, histologically node negative and PCR node negative suggesting that 10 of 29 patients with intermediate thickness melanoma had no evidence of metastatic disease.

5. 8 of 18 (45%%) patients who were clinically node negative and histologically node negative were found to be PCR node positive, suggesting that upstaging occurred. (Sample #'s 12–19)

6. The positive control cell line was PCR positive (Sample #48) and the 2 negative control cell lines were PCR negative (Sample #'s 47, 49)

EXAMPLE 3

Control Cell Lines

Three established cell lines from the American Type Culture Collection (ATCC; Rockville, Md.) were used for controls: human melanoma-derived cell line SK-Mel-28 (ATCC HTB 72) as a positive control and human breast cancer-derived cell line T47D (ATCC HTB 133) and human lymphoid cell line (K562) as a negative control. All were cultured separately in Dulbecco's Modified Eagle's Medium (DMEM) supplemented with 5% fetal calf serum (Hyclone, Inc., Logan, Utah) for two to three of weeks, then aliquoted to about 1 million cells per tube and stored at −70° C. for future extraction of RNA.

EXAMPLE 4

Node Preparation

The half of each node specimen from Example 1 not used for Control Pathological Evaluation was soaked with calcium and magnesium free PBS in a petri dish. Surrounding connective tissue was trimmed. The remaining tissue was disrupted into single cells by gently scraping with sterile scalpels.

EXAMPLE 5

RNA Extraction

Total RNA was extracted from each of the control cell lines of Example 3 and patient cells from Example 4 with an RNA STAT-60 kit (TEL-TEST"B", INC., Friendswood, Tex.). The cells ($10 \times 10^6$) were placed in 1.0 ml phenol and guanidinium thiocyanate solution and homogenized with an 18G, 1½ inch needle. After adding chloroform, the homogenate separated into two phases. The upper aqueous phase containing RNA was removed and precipitated with isopropanol. The precipitate was washed with 75% ethanol and solubilized in 10 μl TE buffer (10 mM Tris, 1 mM EDTA, pH 8.0).

EXAMPLE 6

Reverse Transcription

Two sets of primer sequences (HTYR1 (SEQ ID No:1) and HTYR2 (SEQ ID No:2), MEL1 (SEQ ID No:3) and MEL2 (SEQ ID No:4) for human tyrosinase were devised from previous publications or sequences available through Genebank. For reverse transcription of tyrosinase mRNA, 1.0 μl total RNA extracted from the cells was dispersed in 9.0 μl of a mixture containing 1×PCR buffer (10 mM Tris-HCl, 50 mM KCl, pH 8.3), 5.0 mM MgCl$_2$, 1.0 mM each of DNTP (DATP, dCTP, dGTP, dTTP), 1 unit RNase inhibitor, 5 units Moloney Murine Leukemia Virus (M-MLV) reverse transcriptase (Perkin-Elmer-Cetus Corp. Norwalk, Conn.), and 75 pmol anti-sense outer primer (HTYR2) (SEQ ID No:2). The sample was overlaid with two drops of mineral oil to prevent evaporation. The reaction tube was placed into a programmable thermal controller (MJ Research, Inc.) and incubated at 42° C. for 45 min. denatured at 99° C. for 5 min. and then immediately moved to an ice bucket.

EXAMPLE 7

Polymerase Chain Reaction

The following PCR1 mixture (20 µl) for the extension of the outer primer to obtain a 284 bp cDNA fragment was prepared immediately before use and directly added into each reverse transcription reaction tube: 1×PCR buffer (10 mM Tris-HCl, 50 mM KCl, pH 8.3), 0.625 mM $MgCl_2$, 16.5 µl distilled water, 2.5 units AmpliTaq DNA polymerase (Perkin-Elmer-Cetus Corp. or Promega (Fisher Scientific)), and 75 pmol sense outer primer (HTYRI). Heating at 95° C. for 3 min. was followed by a two-step PCR for 30 cycles (90° C. for 1 min., 62° C. for 1 min. Reaction was concluded at 72° C. for 5 min. to complete the extension.

For reamplification of PCR1 product with nested primers (anti-sense MEL2 (SEQ ID No:4) and sense MEL1 (SEQ ID No:3)) to obtain 207 bp cDNA fragment, 5 µl of 1:50 diluted PCR1 product was amplified in 25 µl final reaction mixture containing 1×PCR buffer (10 mM Tris-HCl, 50 mM KCl, pH 8.3), 1.5 mM $MgCl_2$, 0.8 mM each of dNTP, 2.5 units AmpliTaq polymerase, and 150 pmol each of nested primers. Two drops of mineral oil was also overlaid. The thermal cycle program was identical to PCR1.

To minimize contamination, all the reaction mixtures were prepared in a fume hood. Powder free gloves and aerosol resistant tips were used.

EXAMPLE 8

PCR Products Analysis

Figure 2:
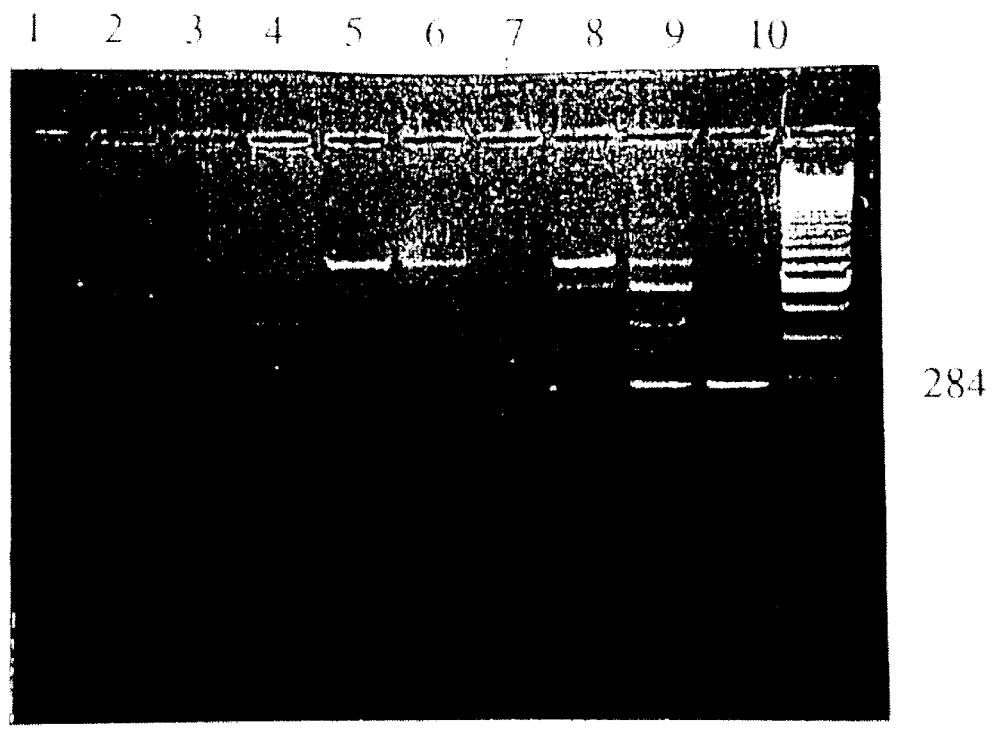
FIG. 2 shows the results of the first round of PCR. A 284 bp band was evident on some of the gels from patients with negative lymph node samples, but with a low density.

The mixture of 9 µl of the PCR1 product or the PCR2 product from Example 7 and 1 µl gel loading solution (Sigma, St. Louis, Mo.) was loaded on 2% agarose gel containing ethidium bromide. A 100 bp ladder (GIBCO BRL, Inc., Grand Island, N.Y.) served as molecular weight marker. A photograph (PCR2, FIG. 1: PCR1, FIG. 2) was taken with Polaroid 667 film by UV transillumination after electrophoresis. A 207 bp tyrosinase gene sequence was detected in lymph node tissue from 19 of the 29 patients. Eight of these patients had previously been found to have negative lymph nodes by routine pathology (Example 1). Table 1 is a record of these results and compares these results to the results obtained utilizing other procedures. A plus (+) sign indicates the presence of melanoma cells; a minus (−) sign indicates the absence of melanoma cells.

EXAMPLE 9

Product Analysis—Restriction Enzyme Mapping

Figure 5:
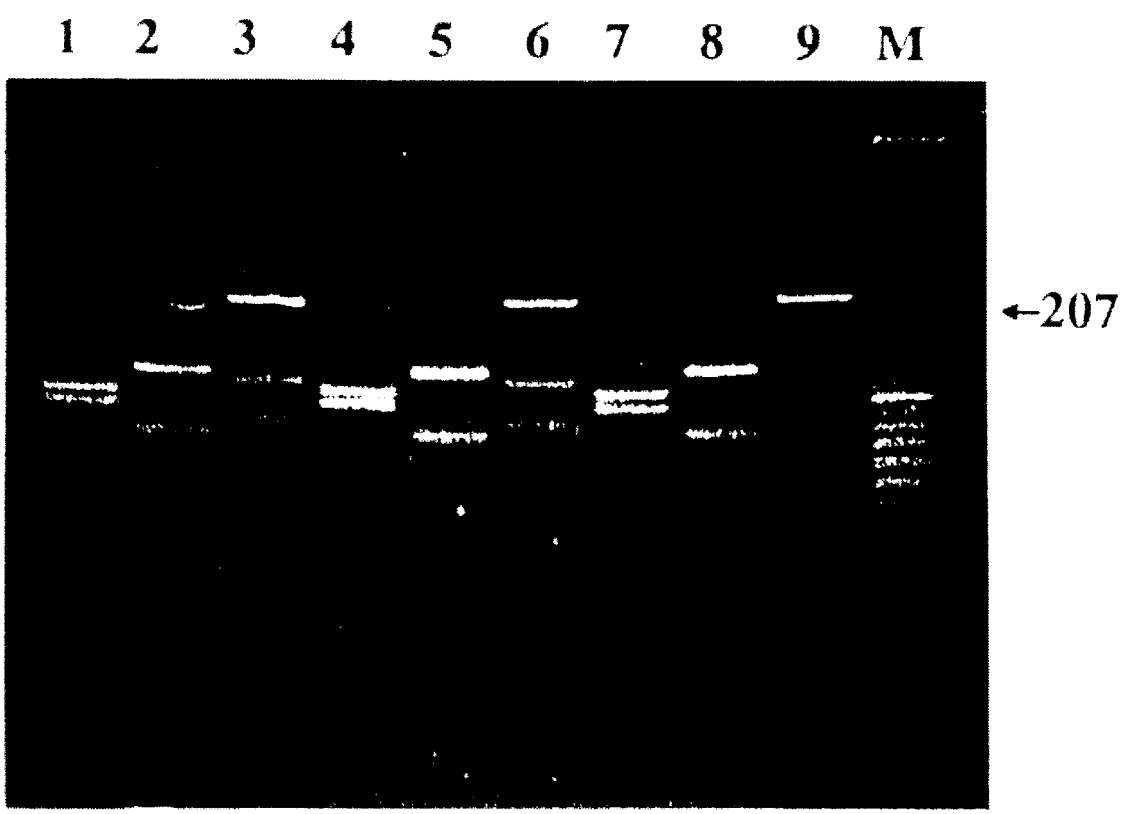
FIG. 5 shows the results of restriction enzyme mapping. RT-PCR2 from 3 different patient samples (Sample #'s 12–14) were digested by 3 different restriction enzymes. Lanes 1, 4, and 7 show the bands of PCR products digested by DdeI. Lanes 2, 5, and 8 show the bands of PCR products digested by HinfI. Lanes 3, 6 and 9 show the bands of PCR products digested by PvuII. Molecular marker is a 100 bp ladder. Lanes 1–3 are PCR products from 1 patient cut with the different restriction enzymes (Sample #12). Likewise, lanes 4–6 (Sample #13) and lanes 7–9 (Sample #14) are from the same patients cut with the three different enzymes.

Mapping with restriction enzymes was used to determine if the PCR product was obtained from tyrosinase mRNA. Three different restriction enzymes (DdeI, HinfI and PvuII) were used to digest RT-PCR2 products from example 7. Twenty units each of the enzymes were incubated at 37° C. for 2 hr to digest 10 µl RT-PCR2 products in 20 µl reaction mixture. The sequence of tyrosinase mRNA is known and the size of fragments obtained with these enzymes can be predicted. Following digestion, the resulting fragments were analyzed on a 2% agarose gel as described for PCR products above and compared with the cutpoint anticipated for the described tyrosinase sequence. FIG. 5 shows the results of this treatment and illustrates that the cut fragments of the 3 patient samples are identical and the same as the base pair length anticipated for the tyrosinase gene. The restriction enzyme mapping confirmed that the RT-PCR2 products are from tyrosinase gene.

EXAMPLE 10

Method Sensitivity

Figure 4:
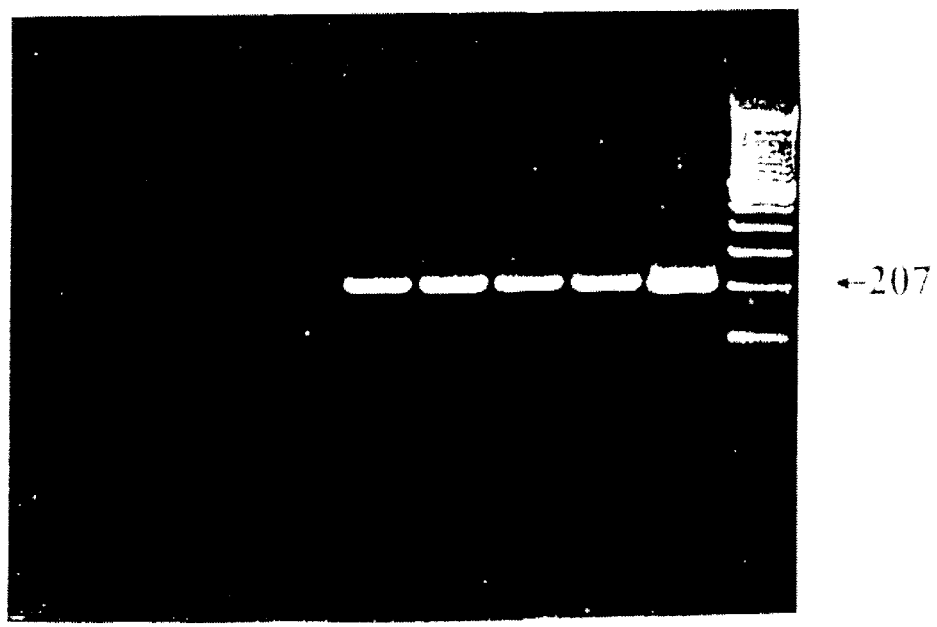
FIG. 4 shows spiking experiment results. Different numbers of SK-Mel-28 melanoma cells were added to normal lymphocytes. Cell ratios: melanoma cell:normal lymphocytes. Lane 1, blank. Lane 2, 10 million normal lymphocytes only. Lane 3, $1:10\times10^6$. Lane 4, $2:10\times10^6$. Lane 5, $3:10\times10^6$. Lane 6, $4:10\times10^6$. Lane 7, $5:10\times10^6$. Lane 8, $10:10\times10^6$. Lane 9, positive control SK-Mel-28 melanoma cells.

Additional experiments were performed to determine the sensitivity of this method. Decreasing numbers of SK-Mel-28 melanoma cells were added to $10×10^6$ lymphocytes isolated from a histologically normal node from a patient with no history of melanoma. The RT-PCR method was able to detect approximately 1 melanoma cell in $10^6$ cells (FIG. 4).

EXAMPLE 11

β-Actin Reverse Transcription

Figure 3:
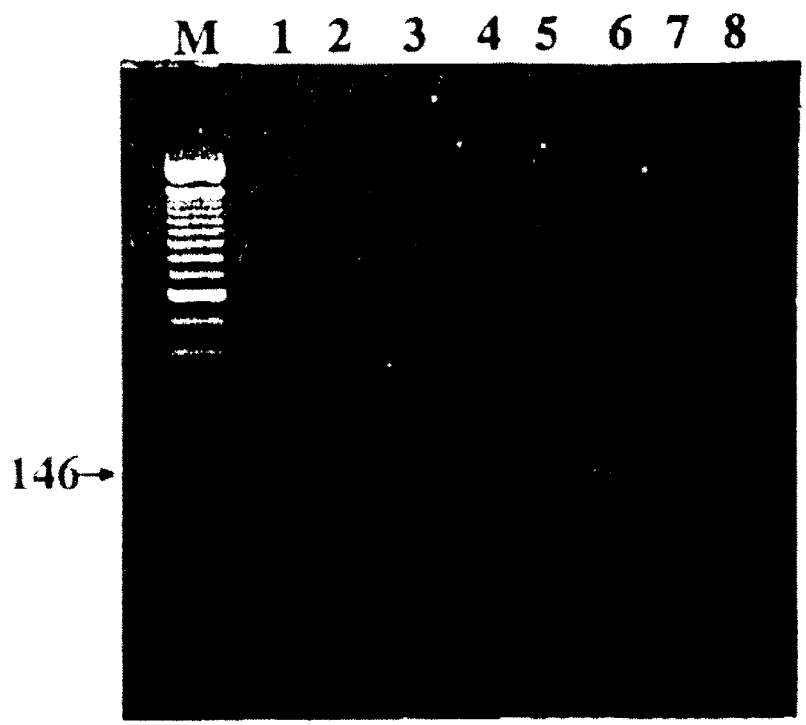
FIG. 3 shows β-actin RT-PCR1 results from tyrosinase RT-PCR2 negative samples (Sample #'s 20–24). Molecular weight marker, 100 bp molecular ladder. Lane 1, blank (no RNA added). Lane 2, breast cancer cell line T47D (Sample #47). Lane 3 to 7, samples from tyrosinase RT-PCR2 negative patients (Sample #'s 20–24).

One set of primer sequences for human β-actin cDNA was devised from previous publications or sequences available through Genebank. The identical reaction mixture and incubation program of Example 6 used to reverse transcribe tyrosinase mRNA was used to reverse transcribe β-actin mRNA except that the primer was β-actin downstream primer (BAD). β-actin cDNA fragment was amplified with the method of Example 7 except that the primers for tyrosinase gene were replaced by β-actin gene primers.

β-actin mRNA was successfully reverse transcribed and amplified from all the tyrosinase gene negative samples. This indicated the RNA in all the samples was undegraded (FIG. 3).

EXAMPLE 12

No RT Polymerase Chain Reaction

Double PCR without RT (NO-RT-PCR) was carried out to ensure that the amplified sequence was from cDNA but not from genomic DNA. All the samples with detectable tyrosinase gene (Sample #'s 1–19) were examined by NO-RT-PCR. None of these was positive, indicating that the samples did not contain genomic DNA. Reaction buffer for NO-RT-PCR1 was the combination of RT and PCR1 reaction mixture except the RNase inhibitor and reverse transcriptase were substituted by equal volumes of distilled water. The amplification program was the same.

TABLE 2

Primer Sequences

| Name | Sequence | Type |
|---|---|---|
| HTYR1 (SEQ ID No:1) | 5'-TTGGCAGATTGTCTGTAGCC-3' | outer, sense |
| HTYR2 (SEQ ID No:2) | 5'-AGGCATTGTGCATGCTGCTT-3' | outer, antisense |
| MEL1 (SEQ ID No:3) | 5'-GTCTTTATGCAATGGAAC-3' | nested, sense |

TABLE 2-continued

Primer Sequences

| Name | Sequence | Type |
|---|---|---|
| MEL2 (SEQ ID No:4) | 5'-GCTATCCCAGTAAGTGGA-3' | nested, antisense |

What is claimed is:

1. A method for determining the presence of melanocytes in lymph node tissue comprising
   a) extracting mRNA from lymph node tissue;
   b) producing cDNA from any mRNA present;
   c) increasing the quantity of any tyrosinase cDNA present; and
   d) determining the presence of tyrosinase cDNA whereby the presence of melanocytes is indicated by the presence of the tyrosinase cDNA.

2. The method of claim 1 where the cDNA is produced using reverse transcriptase and the quantity of tyrosinase cDNA present is increased using polymerase chain reaction.

3. The method of claim 2 where the polymerase chain reaction is a two step polymerase chain reaction using nested primers in the second step.

4. The method of claim 3 where the nested primers are MEL1 (SEQ ID No:3) and MEL2 (SEQ ID No:4).

5. A method for determining the presence of metastatic melanoma in a patient comprising
   a) extracting mRNA from tissue obtained from at least one lymph node of the patient;
   b) producing cDNA from any mRNA present using reverse transcriptase;
   c) amplifying any tyrosinase cDNA present using polymerase chain reaction; and
   d) electrophoresing the product of step c to determine the presence of tyrosinase cDNA whereby the presence of metastatic melanoma is indicated by the presence of the tyrosinase cDNA.

6. The method of claim 2 wherein
   step d further comprises electrophoresing the product of step c to determine the presence of tyrosinase cDNA.

7. A method of determining the spread of a metastatic melanoma from lymph node tissue of a patient comprising
   a) determining the patient's lymph drainage basins proximate to the melanoma;
   b) extracting mRNA from tissue obtained from at least two lymph nodes of the drainage basin determined in step a;
   c) producing cDNA from any mRNA present;
   d) amplifying any tyrosinase cDNA present;
   e) determining the presence of tyrosinase cDNA in the product of step d; and
   f) correlating the absence or presence of tyrosinase cDNA with the location of the patients lymph node whereby absence of tyrosinase cDNA indicates no metastatic melanoma in the lymph drainage basin and presence of tyrosinase cDNA indicates presence of metastatic melanoma in the lymph drainage basin.

8. A method for determining the presence of metastatic melanoma in a patient comprising:
   a) extracting mRNA from tissue obtained from at least one lymph node of the patient;
   b) producing cDNA from any mRNA obtained using reverse transcriptase;
   c) amplifying any tyrosinase cDNA present using a multiple step polymerase chain reaction using nested primers; and
   d) electrophoresing the product of step c to determine the presence of tyrosinase cDNA whereby the presence of metastatic melanoma is indicated by the presence of the tyrosinase cDNA.

9. A method for determining the stage of malignant melanoma in a patient with malignant melanoma by:
   (a) determining the patient's lymph drainage basins and the sentinel node proximate to the melanoma;
   (b) clinically and histologically examining tissue from the sentinel node whereby presence of melanoma cells referred to as histologically node positive, and absence of melanoma cells referred to as histologically node negative, is determined;
   (c) extracting MRNA from tissue obtained from at least the sentinel node and at least one other lymph node of the drainage basin determined in step (a);
   (d) producing cDNA from the extracted mRNA;
   (e) identifying any tyrosinase cDNA present by amplifying using a multiple step polymerase chain reaction using nested primers specific for tyrosinase cDNA whereby absence of tyrosinase cDNA indicates no metastatic melanoma in the lymph drainage basin referred to as PCR node negative, and presence of tyrosinase cDNA indicates presence of metastatic melanoma in the lymph drainage basin referred to as PCR node positive; and
   (f) determining the stage of malignant melanoma wherein patients are staged as being histologically node negative and PCR node negative; histologically node positive and PCR node negative; and histologically and PCR node positive.

* * * * *